(12) United States Patent
Nabeta

(10) Patent No.: US 10,842,770 B2
(45) Date of Patent: *Nov. 24, 2020

(54) NON-AQUEOUS TAXANE PRO-EMULSION FORMULATIONS AND METHODS OF MAKING AND USING THE SAME

(75) Inventor: Kiichiro Nabeta, Setagaya-ku (JP)

(73) Assignee: Teikoku Pharma USA, Inc., San Jose, CA (US)

( * ) Notice: Subject to any disclaimer, the term of this patent is extended or adjusted under 35 U.S.C. 154(b) by 97 days.

This patent is subject to a terminal disclaimer.

(21) Appl. No.: 13/098,031

(22) Filed: Apr. 29, 2011

(65) Prior Publication Data

US 2011/0269829 A1 Nov. 3, 2011

Related U.S. Application Data

(60) Provisional application No. 61/330,705, filed on May 3, 2010.

(51) Int. Cl.
| | | |
|---|---|---|
| *A61K 31/337* | (2006.01) | |
| *A61K 9/107* | (2006.01) | |
| *A61K 47/44* | (2017.01) | |
| *A61K 47/26* | (2006.01) | |

(52) U.S. Cl.
CPC .......... *A61K 31/337* (2013.01); *A61K 9/1075* (2013.01); *A61K 47/26* (2013.01); *A61K 47/44* (2013.01)

(58) Field of Classification Search
None
See application file for complete search history.

(56) References Cited

U.S. PATENT DOCUMENTS

| | | |
|---|---|---|
| 4,814,470 A | 3/1989 | Colin et al. |
| 5,399,363 A | 3/1995 | Liversidge et al. |
| 5,403,858 A | 4/1995 | Bastard et al. |
| 5,407,683 A | 4/1995 | Shively |
| 5,415,869 A | 5/1995 | Straubinger et al. |
| 5,438,072 A | 8/1995 | Bobee et al. |
| 5,439,686 A | 8/1995 | Desai et al. |
| 5,498,421 A | 3/1996 | Grinstaff et al. |
| 5,560,933 A | 10/1996 | Soon-shiong et al. |
| 5,607,690 A | 3/1997 | Akazawa |
| 5,616,330 A | 4/1997 | Kaufman et al. |
| 5,626,867 A | 5/1997 | Eibi et al. |
| 5,698,582 A | 12/1997 | Bastart et al. |
| 5,714,512 A | 2/1998 | Bastart et al. |
| 5,723,635 A | 3/1998 | Durand et al. |
| 5,733,888 A | 3/1998 | Carver et al. |
| 5,750,561 A | 5/1998 | Bastart et al. |
| 5,770,222 A | 6/1998 | Unger et al. |
| 5,785,976 A | 7/1998 | Westesen et al. |
| 5,858,410 A | 1/1999 | Muller et al. |
| 5,877,205 A | 3/1999 | Andersson |
| 5,902,610 A | 5/1999 | Hausheer et al. |
| 5,925,669 A | 7/1999 | Katz et al. |
| 5,929,030 A | 7/1999 | Hamied et al. |
| 5,965,603 A | 10/1999 | Johnson et al. |
| 5,968,972 A | 10/1999 | Broder et al. |
| 5,972,992 A | 10/1999 | Carver et al. |
| 5,977,164 A | 11/1999 | Carver et al. |
| 6,008,385 A | 12/1999 | Durand et al. |
| 6,017,948 A | 1/2000 | Rubinfeld et al. |
| 6,022,985 A | 2/2000 | Authelin et al. |
| 6,071,952 A | 6/2000 | Owens et al. |
| 6,090,844 A | 7/2000 | Han et al. |
| 6,090,955 A | 7/2000 | Reszka et al. |
| 6,096,331 A | 8/2000 | Desai et al. |
| 6,107,333 A | 8/2000 | Andersson |
| 6,118,011 A | 9/2000 | Mayhew et al. |
| 6,121,234 A | 9/2000 | Benet et al. |
| 6,121,245 A | 9/2000 | Firshein |
| 6,121,313 A | 9/2000 | Gao et al. |
| 6,136,846 A | 10/2000 | Rubinfeld et al. |
| 6,153,644 A | 11/2000 | Owens et al. |
| 6,197,980 B1 | 3/2001 | Durand et al. |
| 6,207,178 B1 | 3/2001 | Westesen et al. |
| 6,218,374 B1 | 4/2001 | Rubinfield |
| 6,231,887 B1 | 5/2001 | Gao et al. |
| 6,267,985 B1 | 7/2001 | Chen et al. |
| 6,284,268 B1 | 9/2001 | Mishra et al. |
| 6,294,192 B1 | 9/2001 | Patel et al. |
| 6,334,445 B1 | 1/2002 | Mettinger |

(Continued)

FOREIGN PATENT DOCUMENTS

| | | |
|---|---|---|
| CN | 101244053 A | 2/2007 |
| CN | 100998560 A | 7/2007 |

(Continued)

OTHER PUBLICATIONS

Chen, Jie, "Preparation, Characterization and In Vitro Evaluation of Solid Dispersions Containing Docetaxel," Drug Development and Industrial Pharmacy (2008), 34(6):588-594.

Dev et al., "Isolation and characterization of impurities in docetaxel," Journal of Pharmaceutical and Biomedical Analysis (2006), 40(3):614-622.

Diaz et al., "Changes in microtubule protofilament number induced by Taxol binding to an easily accessible site. Internal microtubule dynamics," Journal of Biological Chemistry (1998), 273(50):33803-33810.

Ekins et al,. "Accelerated Communication, A pharmacophore for human pregnane X receptor ligands," Drug Metabolism and Disposition (2002), 30(1):96-99.

Gentile et al., "Synthesis of dimeric and tetrameric macrolactams with cytotoxic activity," Canadian Journal of Chemistry (2000), 78(6):925-934.

(Continued)

*Primary Examiner* — Bong-Sook Baek
(74) *Attorney, Agent, or Firm* — Foley & Lardner LLP

(57) ABSTRACT

Non-aqueous taxane pro-emulsion formulations are provided. Pro-emulsion formulations of embodiments of the invention include a taxane, an oil component, a surfactant component and, optionally, a non-aqueous solvent component. Also provided are methods of making and using the pro-emulsion formulations, as well as kits that include the pro-emulsion formulations.

13 Claims, No Drawings

(56) References Cited

U.S. PATENT DOCUMENTS

| | | |
|---|---|---|
| 6,346,233 B1 | 2/2002 | Knight et al. |
| 6,348,215 B1 | 2/2002 | Straubinger et al. |
| 6,348,491 B1 | 2/2002 | Chu et al. |
| 6,391,832 B2 | 5/2002 | Lyons et al. |
| 6,436,430 B1 | 8/2002 | Mulye |
| 6,451,339 B2 | 9/2002 | Patel et al. |
| 6,458,373 B1 | 10/2002 | Lambert et al. |
| 6,500,461 B2 | 12/2002 | Perkins et al. |
| 6,506,405 B1 | 1/2003 | Desai et al. |
| 6,509,370 B1 | 1/2003 | Joshi-Hangal et al. |
| 6,531,139 B1 | 3/2003 | Gao et al. |
| 6,537,579 B1 | 3/2003 | Desai et al. |
| 6,538,019 B1 | 3/2003 | Nakajima et al. |
| 6,538,020 B2 | 3/2003 | Joshi-Hangal et al. |
| 6,605,298 B1 | 8/2003 | Leigh et al. |
| 6,610,317 B2 | 8/2003 | Straub et al. |
| 6,638,522 B1 | 10/2003 | Mulye |
| 6,638,973 B2 | 10/2003 | Holton |
| 6,660,286 B1 | 12/2003 | Lambert et al. |
| 6,667,048 B1 | 12/2003 | Lambert et al. |
| 6,720,001 B2 | 4/2004 | Chen et al. |
| 6,727,280 B2 | 4/2004 | Palepu et al. |
| 6,749,868 B1 | 6/2004 | Desai et al. |
| 6,753,006 B1 | 6/2004 | Desai et al. |
| 6,761,901 B1 | 7/2004 | Betageri et al. |
| 6,761,903 B2 | 7/2004 | Chen et al. |
| 6,815,642 B2 | 11/2004 | Haag |
| 6,828,346 B2 | 12/2004 | Joshi-Hangal et al. |
| 6,838,569 B2 | 1/2005 | Sharma et al. |
| 6,932,983 B1 | 8/2005 | Straub et al. |
| 6,964,946 B1 | 11/2005 | Gutierrez-Rocca et al. |
| 6,979,456 B1 | 12/2005 | Parikh et al. |
| 6,982,282 B2 | 1/2006 | Lambert et al. |
| 7,030,155 B2 | 4/2006 | Lambert et al. |
| 7,060,285 B2 | 6/2006 | Muller |
| 7,064,201 B2 | 6/2006 | Hayashi et al. |
| 7,074,821 B1 | 7/2006 | Bouchard et al. |
| 7,101,568 B2 | 9/2006 | Dang et al. |
| 7,345,093 B2 | 3/2008 | Augustine et al. |
| 7,387,623 B2 | 6/2008 | Macleod |
| 7,387,791 B2 | 6/2008 | Betagari et al. |
| RE40,493 E | 9/2008 | Straub et al. |
| 7,446,126 B2 | 11/2008 | Gabetta et al. |
| 7,662,980 B2 | 2/2010 | Liao et al. |
| 7,674,903 B2 | 3/2010 | Hayashi et al. |
| 7,744,909 B2 | 6/2010 | Muller |
| 7,771,751 B2 | 8/2010 | Desai et al. |
| 7,838,551 B2 | 11/2010 | Santini et al. |
| 7,919,113 B2 | 4/2011 | Domb |
| 7,919,497 B2 | 4/2011 | Palladino et al. |
| 7,935,704 B2 | 5/2011 | Palladino et al. |
| 7,956,058 B2 | 6/2011 | Hayashi et al. |
| 8,044,093 B2 | 10/2011 | Hao |
| 8,163,940 B2 | 4/2012 | Pyo et al. |
| 8,318,957 B2 | 11/2012 | Gabetta et al. |
| 2001/0029264 A1 | 10/2001 | McChesney-Harris |
| 2002/0013298 A1 | 1/2002 | Hunter |
| 2002/0034537 A1 | 3/2002 | Schulze et al. |
| 2002/0058616 A1 | 5/2002 | Broder et al. |
| 2002/0102280 A1 | 8/2002 | Anderson |
| 2002/0141966 A1 | 10/2002 | Dang |
| 2003/0099674 A1 | 5/2003 | Chen |
| 2003/0133955 A1 | 7/2003 | Desai et al. |
| 2003/0133984 A1 | 7/2003 | Ambuhl et al. |
| 2003/0158249 A1* | 8/2003 | Chi et al. ............... 514/449 |
| 2003/0207936 A1 | 11/2003 | Chen |
| 2003/0219472 A1 | 11/2003 | Pauletti et al. |
| 2004/0092428 A1* | 5/2004 | Chen et al. ............... 514/2 |
| 2004/0105778 A1 | 6/2004 | Lee et al. |
| 2004/0122081 A1 | 6/2004 | Gogate et al. |
| 2004/0219214 A1 | 11/2004 | Gravett et al. |
| 2004/0220081 A1 | 11/2004 | Kreitz et al. |
| 2005/0025792 A1 | 2/2005 | Peracchia et al. |
| 2005/0070496 A1 | 3/2005 | Borovac et al. |
| 2005/0090667 A1 | 4/2005 | Hayashi et al. |
| 2005/0197344 A1 | 9/2005 | Palladino et al. |
| 2006/0067952 A1 | 3/2006 | Chen |
| 2006/0079571 A1 | 4/2006 | Gabetta et al. |
| 2006/0188566 A1 | 8/2006 | Liversidge et al. |
| 2006/0210622 A1 | 9/2006 | Pace et al. |
| 2006/0217553 A1 | 9/2006 | Hayashi et al. |
| 2006/0223822 A1 | 10/2006 | Hayashi et al. |
| 2006/0223823 A1 | 10/2006 | Hayashi et al. |
| 2006/0241170 A1 | 10/2006 | Soon-Shiong et al. |
| 2006/0292186 A1 | 12/2006 | Garrigue et al. |
| 2007/0078138 A1 | 4/2007 | Palladino et al. |
| 2007/0082838 A1 | 4/2007 | De et al. |
| 2007/0117744 A1 | 5/2007 | Desai et al. |
| 2007/0142457 A1 | 6/2007 | Pontiroli et al. |
| 2007/0196361 A1 | 8/2007 | Soon-Shiong et al. |
| 2007/0225510 A1 | 9/2007 | Henri et al. |
| 2007/0264349 A1 | 11/2007 | Lee et al. |
| 2008/0045584 A1 | 2/2008 | Chi et al. |
| 2008/0051450 A1 | 2/2008 | Santini et al. |
| 2008/0057129 A1 | 3/2008 | Lerner et al. |
| 2008/0064760 A1 | 3/2008 | Li et al. |
| 2008/0108693 A1 | 5/2008 | Liao et al. |
| 2008/0146651 A1* | 6/2008 | Jee ..................... A61K 9/10 514/449 |
| 2008/0167369 A1 | 7/2008 | Gabetta et al. |
| 2008/0187595 A1 | 8/2008 | Jordan et al. |
| 2008/0200700 A1 | 8/2008 | Gabetta et al. |
| 2008/0220074 A1 | 9/2008 | Bosch et al. |
| 2008/0262078 A1 | 10/2008 | Namdeo et al. |
| 2008/0300297 A1 | 12/2008 | Kysilka |
| 2008/0319048 A1 | 12/2008 | Palepu et al. |
| 2009/0011005 A1 | 1/2009 | Zago et al. |
| 2009/0011009 A1 | 1/2009 | Benita et al. |
| 2009/0018353 A1 | 1/2009 | Pyo et al. |
| 2009/0118354 A1 | 5/2009 | Liu et al. |
| 2009/0130198 A1 | 5/2009 | Hao et al. |
| 2009/0143997 A1 | 6/2009 | Yaffe et al. |
| 2009/0156660 A1 | 6/2009 | Svoboda et al. |
| 2009/0156828 A1 | 6/2009 | Henri et al. |
| 2009/0163574 A1 | 6/2009 | Kim et al. |
| 2009/0215882 A1 | 8/2009 | Bouzada et al. |
| 2009/0221688 A1 | 9/2009 | Machado et al. |
| 2009/0238878 A1 | 9/2009 | Singh |
| 2009/0275647 A1* | 11/2009 | Sehgal ................ A61K 9/0019 514/449 |
| 2009/0275762 A1 | 11/2009 | Liao et al. |
| 2009/0298926 A1 | 12/2009 | Gabetta et al. |
| 2009/0306400 A1 | 12/2009 | Henri et al. |
| 2010/0034749 A1 | 2/2010 | Schulze et al. |
| 2010/0069643 A1 | 3/2010 | McChesney et al. |
| 2010/0099879 A1 | 4/2010 | Benovsky et al. |
| 2010/0099897 A1 | 4/2010 | Kim et al. |
| 2010/0111830 A1 | 5/2010 | Boyden et al. |
| 2010/0111831 A1 | 5/2010 | Boyden et al. |
| 2010/0111837 A1 | 5/2010 | Boyden et al. |
| 2010/0111841 A1 | 5/2010 | Boyden et al. |
| 2010/0111842 A1 | 5/2010 | Boyden et al. |
| 2010/0111843 A1 | 5/2010 | Boyden et al. |
| 2010/0111844 A1 | 5/2010 | Boyden et al. |
| 2010/0111845 A1 | 5/2010 | Boyden et al. |
| 2010/0111846 A1 | 5/2010 | Boyden et al. |
| 2010/0111847 A1 | 5/2010 | Boyden et al. |
| 2010/0111848 A1 | 5/2010 | Boyden et al. |
| 2010/0111849 A1 | 5/2010 | Boyden et al. |
| 2010/0111850 A1 | 5/2010 | Boyden et al. |
| 2010/0111854 A1 | 5/2010 | Boyden et al. |
| 2010/0111855 A1 | 5/2010 | Boyden et al. |
| 2010/0111938 A1 | 5/2010 | Boyden et al. |
| 2010/0112067 A1 | 5/2010 | Boyden et al. |
| 2010/0112068 A1 | 5/2010 | Boyden et al. |
| 2010/0113614 A1 | 5/2010 | Boyden et al. |
| 2010/0113615 A1 | 5/2010 | Boyden et al. |
| 2010/0114267 A1 | 5/2010 | Boyden et al. |
| 2010/0114268 A1 | 5/2010 | Boyden et al. |
| 2010/0114496 A1 | 5/2010 | Boyden et al. |
| 2010/0114497 A1 | 5/2010 | Boyden et al. |
| 2010/0114546 A1 | 5/2010 | Boyden et al. |
| 2010/0119557 A1 | 5/2010 | Boyden et al. |
| 2010/0121466 A1 | 5/2010 | Boyden et al. |

(56) References Cited

U.S. PATENT DOCUMENTS

| | | |
|---|---|---|
| 2010/0143243 A1 | 6/2010 | Boyden et al. |
| 2010/0145080 A1 | 6/2010 | Johnson et al. |
| 2010/0152651 A1 | 6/2010 | Boyden et al. |
| 2010/0152880 A1 | 6/2010 | Boyden et al. |
| 2010/0160653 A1 | 6/2010 | Palle et al. |
| 2010/0163576 A1 | 7/2010 | Boyden et al. |
| 2010/0166872 A1 | 7/2010 | Singh et al. |
| 2010/0168900 A1 | 7/2010 | Boyden et al. |
| 2010/0185174 A1 | 7/2010 | Boyden et al. |
| 2010/0187728 A1 | 7/2010 | Boyden et al. |
| 2010/0197776 A1 | 8/2010 | Didier et al. |
| 2010/0197944 A1 | 8/2010 | Palle et al. |
| 2010/0267818 A1 | 10/2010 | Yoo et al. |
| 2010/0286254 A1 | 11/2010 | Blatter et al. |
| 2010/0297244 A1 | 11/2010 | Khopade et al. |
| 2010/0311825 A1 | 12/2010 | Rortais et al. |
| 2011/0002851 A1 | 1/2011 | Haas et al. |
| 2011/0082193 A1 | 4/2011 | Kysilka |
| 2011/0105598 A1 | 5/2011 | Gurjar et al. |
| 2011/0112036 A1 | 5/2011 | Demeule et al. |
| 2011/0118199 A1 | 5/2011 | Dormeyer |
| 2011/0130446 A1 | 6/2011 | Parente Duena et al. |
| 2011/0150765 A1 | 6/2011 | Boyden et al. |
| 2011/0152360 A1 | 6/2011 | Liu et al. |
| 2011/0159111 A1 | 6/2011 | Curry et al. |
| 2011/0189125 A1 | 8/2011 | George et al. |
| 2011/0195030 A1 | 8/2011 | Mumper et al. |
| 2011/0196026 A1 | 8/2011 | De et al. |
| 2011/0206739 A1 | 8/2011 | Nicolosi et al. |
| 2011/0245260 A1 | 10/2011 | Palladino et al. |
| 2011/0275705 A1 | 11/2011 | Daftary et al. |
| 2011/0275841 A1 | 11/2011 | Kadaboina et al. |
| 2011/0293745 A1 | 12/2011 | Hoch et al. |
| 2012/0058151 A1 | 3/2012 | Gonzalez Ferreiro et al. |
| 2012/0071674 A1 | 3/2012 | Cieslinski |
| 2012/0087959 A1 | 4/2012 | Khopade et al. |
| 2012/0101738 A1 | 4/2012 | Boyden et al. |
| 2012/0109613 A1 | 5/2012 | Boyden et al. |
| 2012/0128783 A1 | 5/2012 | Boyden et al. |
| 2012/0157517 A1 | 6/2012 | Chen et al. |
| 2012/0164069 A1 | 6/2012 | Boyden et al. |
| 2012/0164072 A1 | 6/2012 | Linder et al. |
| 2012/0225118 A1 | 9/2012 | Chen et al. |
| 2012/0295802 A1 | 11/2012 | Yaffe et al. |
| 2013/0052241 A1 | 2/2013 | Nabeta |

FOREIGN PATENT DOCUMENTS

| | | |
|---|---|---|
| CN | 101525321 | 9/2009 |
| EP | 1479382 A1 | 11/2004 |
| JP | 04-164024 A | 6/1992 |
| JP | 2595458 B2 | 1/1997 |
| JP | 09-507233 A | 7/1997 |
| JP | 2010-270023 | 12/2010 |
| JP | 4734910 B2 | 5/2011 |
| WO | WO 93/23389 A1 | 11/1993 |
| WO | WO 94/18954 A1 | 9/1994 |
| WO | WO 94/20072 A1 | 9/1994 |
| WO | WO 98/30205 A1 | 7/1998 |
| WO | WO 99/00113 A1 | 1/1999 |
| WO | WO 99/56727 A2 | 11/1999 |
| WO | WO 00/32186 A3 | 6/2000 |
| WO | WO 00/33862 A1 | 6/2000 |
| WO | WO 00/78247 A1 | 12/2000 |
| WO | WO 01/30448 A1 | 5/2001 |
| WO | WO 01/72299 A1 | 10/2001 |
| WO | WO 01/076561 A3 | 10/2001 |
| WO | WO 2004/105737 A3 | 12/2004 |
| WO | WO 2007/096900 A1 | 8/2007 |
| WO | WO 2008/026048 A3 | 3/2008 |
| WO | WO 2008/087076 A1 | 7/2008 |
| WO | WO 2008/102374 A1 | 8/2008 |
| WO | WO 2008/114274 A1 | 9/2008 |
| WO | WO 2009/004188 A3 | 1/2009 |
| WO | WO 2009/043226 A1 | 4/2009 |
| WO | WO 2009/047794 * | 4/2009 |
| WO | WO 2009/123595 A1 | 10/2009 |
| WO | WO 2010/023321 A1 | 3/2010 |
| WO | WO 2011/081373 A2 | 7/2011 |
| WO | WO 2012/160568 A1 | 11/2012 |

OTHER PUBLICATIONS

Han et al., "Phytantriol-based inverted type bicontinuous cubic phase for vascular embolization and drug sustained release," European Journal of Pharmaceutical Sciences (2010), 41(5):692-699.

Harper et al., "13C NMR Investigation of Solid-State Polymorphism in 10-Deacetyl Baccatin III," Journal of the American Chemical Society (2002), 124(35):10589-10595.

Jimenez-Barbero et al., "The solid state, solution and tubulin-bound conformations of agents that promote microtubule stabilization," Current Medicinal Chemistry: Anti-Cancer Agents (2002), 2(1):91-122.

Johnson et al., 12,13-Isotaxanes: Synthesis of New Potent Analogs and X-ray Crystallographic Confirmation of Structure, Journal of Medicinal Chemistry (1997), 40(18), 2810-2812 CODEN: JMCMAR; ISSN: 0022-2623.

Juarez-Guerra et al., "Addition reaction of benzylbenzylideneamine to lithium enolates of 1,3-dioxolan-4-one: synthesis of 2-phenylisoserines," ARKIVOC (2011), (9):354-366.

Lucatelli et al., "Synthesis of C-3' Methyl Taxotere (Docetaxel)," Journal of Organic Chemistry (2002), 67(26):9468-9470.

Muller et al., "'Abnormal' eight-membered ring formation through SN2' intramolecular Nozaki/Kishi reaction in a synthetic approach to a taxane precursor," Tetrahedron Letters (1998), 39(3/4):279-282.

Naik et al., "Preparation of PEGylated liposomes of docetaxel using supercritical fluid technology," Journal of Supercritical Fluids (2010), 54(1):110-119.

Perrin, M.A., "Crystallography of drug polymorphism: emergence of new resolution methods and prediction of crystalline structures," Annales Pharmaceutiques Francaises (2002), 60(3):187-202, with English summary on first page.

Qi et al., "A novel method to synthesize docetaxel and its isomer with high yields," Journal of Heterocyclic Chemistry (2005), 42(4):679-684.

Raczko et al., "Asymmetric syn-dihydroxylation of β-substituted (2R)-N-(α,β-enoyl)bornane-10,2-sultams," Helvetica Chimica Acta (1998), 81(7):1264-1277.

Roy et al., "A concise enantioselective synthesis of a fully oxygen substituted ring A Taxol precursor," Tetrahedron (2003), 59(27):5115-5121.

Skariyachan et al., "Design and discovery of novel therapeutic drugs against Helicobacter pylori gastroduodenal cancer by in silico approach," Research Journal of Pharmaceutical, Biological and Chemical Sciences (2010), 1(4):1005-1016.

Skariyachan et al., "In silico investigation and docking studies of E2F3 tumor marker: discovery and evaluation of potential inhibitors for prostate and breast cancer," International Journal of Pharmaceutical Sciences and Drug Research (2010), 2(4):254-260.

Wang et al., "Preparation and evaluation of docetaxel-loaded albumin nanoparticles for intravenous administration," Journal of Chinese Pharmaceutical Sciences (2010), 19(3):214-222.

Zaske et al., "Docetaxel. Solid state characterization by x-ray powder diffraction and thermogravimetry," Journal de Physique IV: Proceedings (2001), 11(Pr10, XXVII JEEP, Journees d'Etude des Equilibres entre Phases, 2001), 221-226.

Kan et al., "Development of nonionic surfactant/phospholipid o/w emulsion as a paclitaxel delivery system," Journal of Controlled Release, 1999, 58:271-278.

U.S. Appl. No. 14/041,675, filed Sep. 30, 2013, Nabeta.
U.S. Appl. No. 14/041,694, filed Sep. 30, 2013, Nabeta.

* cited by examiner

NON-AQUEOUS TAXANE PRO-EMULSION FORMULATIONS AND METHODS OF MAKING AND USING THE SAME

CROSS-REFERENCE TO RELATED APPLICATIONS

Pursuant to 35 U.S.C. § 119 (e), this application claims priority to the filing dates of: U.S. Provisional Patent Application Ser. No. 61/330,705 filed on May 3, 2010; the disclosure of which application is herein incorporated by reference.

INTRODUCTION

Taxanes constitute a family of naturally occurring diterpene compounds including paclitaxel. Paclitaxel, originally isolated from the bark of the Pacific Yew tree (*Taxus brevifolia*), and its semi-synthetic analogue, docetaxel, are two examples of taxane compounds. Taxanes are active agents that block cell growth by stopping mitosis via microtubule interference.

Taxanes can be used effectively to treat a variety of cancers and have been reported to have therapeutic effects in treating certain inflammatory diseases. Paclitaxel, for example, has been found to have activity against ovarian and breast cancers, as well as against malignant melanoma, colon cancer, leukemias and lung cancer (see, e.g., Borman, Chemical & Engineering News, Sep. 2, 1991, pp. 11-18; The Pharmacological Basis of Therapeutics (Goodman Gilman et al., eds.), Pergamon Press, New York (1990), p. 1239: Suffness, Antitumor Alkaloids, in: "The Alkaloids, Vol. XXV," Academic Press, Inc. (1985), Chapter 1, pp. 6-18: Rizzo et al., J. Pharm. & Biomed. Anal. 8(2):159-164 (1990); and Biotechnology 9:933-938 (October, 1991).

Formulation of taxanes in therapeutically useful carriers, so as to enable the taxanes to be administered to animals, is made difficult by the nature of the taxane molecule, which can be poorly soluble in both aqueous and lipid carriers.

SUMMARY

Non-aqueous taxane pro-emulsion formulations are provided. Pro-emulsion formulations include a taxane, an oil component, a surfactant component and, optionally, a non-aqueous solvent component. Also provided are methods of making and using the pro-emulsion formulations, as well as kits that include the pro-emulsion formulations.

DETAILED DESCRIPTION

Non-aqueous taxane pro-emulsion formulations are provided. Pro-emulsion formulations include a taxane, an oil component, a surfactant component and, optionally, a non-aqueous solvent component. Also provided are methods of making and using the pro-emulsion formulations, as well as kits that include the pro-emulsion formulations.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following sections, the pro-emulsion formulations and emulsions prepared therefrom, as well as methods using the same, are described first in greater detail, followed by a review of methods for preparing the pro-emulsion formulations and emulsions, as well as kits that may include the formulations.

Taxane Pro-Emulsion Formulations

Aspects of the invention include taxane pro-emulsion formulations. In some instances, the pro-emulsion formulations are non-aqueous liquid compositions that, upon combination with an aqueous medium, produce a taxane emulsion. The non-aqueous liquid pro-emulsion formulations of embodiments of the invention include at least a taxane, an oil component, a surfactant component and, optionally, a non-aqueous solvent component.

Taxanes of interest are diterpene compounds. In some instances, taxanes are compounds described by the formula:

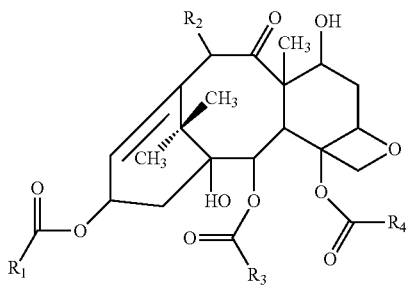

where:

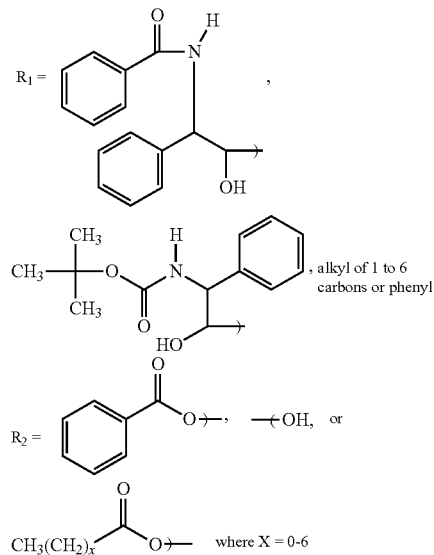

$R_3$ = alkyl of 1 to 6 carbons or phenyl; and
$R_4$ = alkyl of 1 to 6 carbons or phenyl.

Of interest are anhydrous taxanes as well as hydrates thereof, e.g., mono, di, tri, tetra and penta hydrates, etc. In certain embodiments, the taxane is paclitaxel or docetaxel or a hydrate thereof, e.g., docetaxel trihydrate, paclitaxel trihydrate, etc. Taxanes of interest also include, but are not limited to: 7-epitaxol, 7-acetyl taxol, 10-desacetyl-taxol, 10-desacetyl-7-epitaxol, 7-xylosyltaxol, 10-desacetyl-7-glutaryltaxol, 7-N,N-dimethylglycyltaxol, 7-L-alanyltaxol, SB-T-1011, etc. The taxane may be present as a free base or salt.

Pro-emulsion formulations include an effective amount of a taxane. By effective amount is meant a dosage sufficient to provide the desired result, e.g., inhibition of cellular proliferation. The effective amount of taxane may vary depending on the particular taxane employed, and in certain embodiments ranges from 0.05 to 5% by weight, such as 0.5 to 5% by weight and including 0.3 to 3% by weight. In certain embodiments, the pro-emulsion formulations include an effective amount of paclitaxel or paclitaxel trihydrate. In certain embodiments, paclitaxel or paclitaxel trihydrate is present in the pro-emulsion formulation in an amount ranging from 0.05 to 5.0% w/w, such as 0.5 to 5.0% w/w, and including 0.3 to 3.0% w/w, where in some instances the amount ranges from 0.3 to 5.0% w/w, such as 0.3 to 3.0% w/w, e.g., 0.4 to 2.5% w/w, e.g., 0.5 to 2.0% w/w, and including 1.0 to 1.5% w/w. In certain embodiments, the pro-emulsion formulations include an effective amount of docetaxel or docetaxel trihydrate. In certain embodiments, docetaxel or docetaxel trihydrate is present in the pro-emulsion formulation in an amount ranging from 0.1 to 5% w/w, such as 0.5 to 5% w/w and including 0.5 to 3% w/w.

Also present in the pro-emulsion formulations is an oil component made up of one or more oils. Oils of interest are physiologically acceptable and include, but are not limited to: simple lipids, derived lipids, complex lipids that are derived from natural vegetable oil and fat, animal oil and fat, and mineral oil, or mixtures thereof, where the oils may be naturally occurring or synthetic.

In certain embodiments, the oil includes, but is not limited to soybean oil, olive oil, sesame oil, castor oil, corn oil, peanut oil, safflower oil, grape seed oil, eucalyptus oil, medium-chain fatty acid esters, low-chain fatty acid esters, and the like. Animal oils and fat of interest include, but are not limited to, cod-liver oil, seal oil, sardine oil, docosahexiaenoic acid, and eicosapentaenoic acid. Mineral oils of interest include, but are not limited to, liquid paraffins (e.g. oils derived from n-alkanes), naphthenic oils (e.g. oils based on cycloalkanes), and aromatic oils (e.g. oil based on aromatic hydrocarbons). One or a combination of more than one of these types of oils can be used. For example, some embodiments of the subject emulsion formulations include soybean oil, olive oil, sesame oil, or combinations thereof. Other embodiments include soybean oil, olive oil, or combinations thereof. Highly refined oils and fats are employed in certain embodiments.

Oils of interest also include tocopherols. Tocopherols are a family of natural and synthetic compounds, also known by the generic names tocols or Vitamin E. α-tocopherol is the most abundant and active form of this class of compounds and it has the following chemical structure (Scheme I):

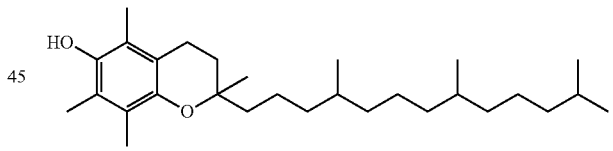

Other members of this class include α-, β-, γ-, and δ-tocotrienols, and α-tocopherol derivatives such as tocopherol acetate, phosphate, succinate, nitotinate and linoleate. Any convenient tocopherol may be present, as desired, including the specific tocopherols listed above.

Oils of interest also include polyol esters of medium chain fatty acids. The term "polyol esters of medium chain fatty acids" is intended to include esters and mixed esters of glycerol, propylene glycol or other open chain polyols such as polyethylene glycol, reacted with medium chain fatty acids, e.g., where the acid has a chain length between 6 and 12 carbon atoms. In some instances, the polyol esters of medium chain fatty acids are triglycerides or diglycerides of the $C_8$-$C_{10}$ fatty acids, e.g., as may be commercially available from the fractionation of coconut oil. Commercially available products of this description are sold under the trade names "Miglyol" and "Captex 300" which are described as having a typical composition of about 68% $C_8$ fatty acid (caprylic) triglyceride and about 28% $C_{10}$ fatty acid (capric) triglyceride with minor levels of $C_6$ and $C_{14}$ fatty acid triglycerides.

In certain embodiments, the oil component is 10% w/w or less of the formulation. In some instances, the amount of oil in the pro-emulsion formulation ranges from 0.05 to 10% w/w, such as 0.1 to 10% or 0.1 to 8% w/w, and including 0.5 to 5% w/w or 5 to 10% w/w. In some instances, the amount of oil by weight is the same as the amount of taxane by weight.

Also present in certain embodiments of the subject pro-emulsion formulations is a surfactant component, which may include one or more surfactants. Surfactants of interest include any type of surfactant that can be used for pharmaceutical formulations. Nonionic surfactants of interest include, but are not limited to, polyoxyalkylene copolymer, and sorbitan fatty acid esters. In some embodiments, the sorbitan fatty acid ester is a polyoxyethylene sorbitan fatty acid ester (e.g., Polyoxyethylene sorbitan tristearate (Tween 65); Polyoxyethylene sorbitan trioleate (Tween 85); Polyethylene glycol 400 monostearate; Polysorbate 60; (Tween 60); Polyoxyethylene monostearate (Myrj 49); Polysorbate 80 (Tween 80); Polysorbate 40 (Tween 40); and Polysorbate 20 (Tween 20)) or sorbitan fatty acid esters (e.g., Sorbitan trioleate (Span 85); Sorbitan tristearate (Span 65); Sorbitan sesquioleate (Arlacel 83); Glyceryl monostearate; Sorbitan monooleate (Span 80); Sorbitan monostearate (Span 60); Sorbitan monopalmitate (Span 40); Sorbitan monolaurate (Span 20)). The amount of surfactant in the pro-emulsion formulation may vary. In some instances, the amount of surfactant in the pro-emulsion formulation is 10% w/w or more, such as 20% w/w or more, 30% w/w or more, 40% w/w or more, or 45% w/w or more. In some instances, the amount of surfactant in the pro-emulsion formulation ranges from 10 to 98% w/w, such as 20 to 98% w/w and including 30 to 98% w/w, e.g., 45 to 98% w/w. In some instances, the amount of surfactant in the pro-emulsion formulation ranges from 30 to 70% w/w, such as 30 to 60% w/w, e.g., 35 to 55% w/w, and including 30 to 50% w/w, e.g., 30 to 40% w/w. The combination ratio by weight of the oil and the surfactant in the subject pro-emulsion formulations may vary, ranging in some instances from 1/1000 to 1/5, such as 1/100 to 1/8, 1/80 to 1/10, 1/50 to 1/16, 1/40 to 1/16, or 1/35 to 1/20.

In some instances, pro-emulsion formulations of the invention further include a non-aqueous solvent component, which may include one or more non-aqueous solvents. Non-aqueous solvents of interest include, but are not limited to: propylene glycol, polypropylene glycol, polyethylene glycol (such as PEG300, 400, 600, 800, 1000, etc., where in certain embodiments polyethylene glycols, when employed, have an average molecular weight of 1000 or less), glycerin, ethanol, triacetin, dimethyl isosorbide, glycofurol, propylene carbonate, dimethyl acetamide or a mixture thereof. The non-aqueous solvent, when present, may be present in varying amounts, and in some instances ranges from 0.1 to 90% by weight, such as 10 to 70% by weight and including 20 to 65% by weight, e.g., 30 to 60%, 35 to 55%, or 40-50% by weight. In some instances, the non-aqueous solvent, when present, may be present in an amount by weight that is 70% or less, such as 60% or less, 50% or less, 40% or less, 30% or less or 20% or less. The combination ratio by weight of the oil and the non-aqueous solvent in the subject pro-emulsion formulations may vary, and in some instances is 1/1000 or greater, such as 1/200 or greater. In some instances, the combination ratio by weight of the oil and the non-aqueous solvent ranges from 1/200 to 1/2, such as 1/100 to 1/2, 1/100 to 1/6, 1/100 to 1/20, 1/80 to 1/30, or 1/60 to 1/40.

In some instances, the pro-emulsion formulation may include an organic acid component. An organic acid component may include an organic acid and/or its conjugate base (or salt thereof), wherein in some instances the organic acid component may include an organic acid and a salt of its conjugate base. Organic acids of interest upon which the organic acid component may be based include lactic acid, acetic acid, citric acid, etc. In some instances, the organic acid component is a lactic acid/sodium lactate component, such that the component includes both lactic acid and sodium lactate. In some instances, the lactic acid/sodium lactate component is present in an amount ranging from about 0.3 to 3% w/w.

Methods of Preparing Taxane Pro-Emulsion Formulations

Pro-emulsion formulations may be prepared according to any convenient protocol. As such, the components of the desired pro-emulsion may be combined under conditions sufficient to produce the desired pro-emulsion. Accordingly, an amount of one or more taxanes, one or more oils, one or more surfactants and one or more non-aqueous solvents may be combined under conditions sufficient to produce a pro-emulsion. The components may be combined in any convenient order. The components may be combined at any convenient temperature, e.g., room temperature or elevated temperatures, such as temperatures ranging from 30 to 95° C., e.g., 50 to 60° C. Certain of the components may be combined with each other, and then combined with the aqueous medium, or all of the components may be combined at substantially the same time. Combination may include various manners of agitation, e.g., stirring, sonication, etc., in order to produce the desired precursor emulsion. Depending on the particular preparation method, an aqueous solvent, e.g., water, etc. may or may not be employed during preparation of the pro-emulsion compositions.

In one embodiment, a pro-emulsion is prepared without an aqueous solvent. In these embodiments, the components of the pro-emulsion, e.g., taxane, oil, surfactant and non-aqueous solvent, are combined, e.g., as described above, Where desired, heat may be employed to facilitate mixing. This resultant pro-emulsion is translucent e.g., as described above.

As indicated above, in some instances, the pro-emulsion preparation protocol includes use of an aqueous solvent, e.g., pure water. In these instances, an initial emulsion composition is prepared that includes a taxane, an oil component, a surfactant component, a non-aqueous solvent component and an aqueous solvent, e.g., water, etc. In certain embodiments, the initial emulsion composition is clear. By clear is meant that the emulsion is a translucent, if not transparent liquid, i.e., the liquid is pellucid. As such, the initial preparation is not cloudy, e.g., as a suspension may appear. Further details regarding the pro emulsions that may be prepared from the taxane initial composition precursors are provided below. In some instances, the particle size of the initial composition ranges from 3 to 70 nm, such as 5 to 50 nm and including 7 to 30 nm, such as 8 to 15 nm. Of interest in certain embodiments are initial compositions that are clear (e.g., as described above) and have a particle size of 70 nm or less, such as 50 nm or less, including 30 nm or less, including 25 nm or less, 20 nm or less and 15 nm or less. In these embodiments, as a final step, water may be removed from the initial emulsion composition to produce a final, non-aqueous pro-emulsion. Removal of water may be accomplished using any convenient protocol, e.g., via a combination of pressure and/or temperature modulation, such as heating.

The preparation methods can be carried out at room temperature or at a temperature lower than room temperature. Specific examples of protocols for preparing pro-emulsions are provided in the Experimental section, below.

Where desired, an amount of the pro-emulsion may be loaded into an individual dosage container, e.g., vial, which holds the pro-emulsion and keeps it sterile during shipping, storage, and handling. Before or during the loading stage, the pro-emulsion can be passed through a sub-micron sterilizing filter, e.g., a 0.2 hydrophilic filter) which has a sufficiently small pore size to remove any bacteria or viruses. As used herein, the term "vial" refers to any stiff-walled container that is used to hold the pro-emulsion formulation. Nearly all pharmaceutical vials are made of clear glass, which allows several advantages, including visual inspection of the enclosed drug (to ensure that it is still in a clean, non-caramelized, non-collapsed form, when it is ready for use) and of the container itself (to ensure that it does not have a hairline crack in one of the walls, which could jeopardize or destroy sterility of the enclosed drug). Various types of pharmaceutical vials are known. Single-chamber vials can be sealed with rubber or plastic plugs that will allow a hypodermic needle to be pushed through the rubber seal. Alternately, a single-chamber vial can be made of a brittle and easily breakable material, inside a sealed bag that can contain an aqueous solution (such as physiological saline or a dextrose solution, in an intravenous infusion bag); if this type of vial is broken, it will release its contents into the still-sealed bag, for mixing. In yet other embodiments, two-chamber vials or analogous structures, e.g., as described in Published United States Application Publication No. 20030099674 and U.S. Pat. No. 4,781,354 may be employed.

Taxane Product Emulsion Formulations and Methods of Use

Following preparation of the pro-emulsion formulation, e.g., as described above, at the time of desired administration to a subject, a dosage amount of the pro-emulsion may be combined with an aqueous medium to prepare a product emulsion formulation that is suitable for use. The dosage amount of the pro-emulsion formulation may be combined with any suitable aqueous medium, where aqueous mediums of interest include, but are not limited to: deionized water, USP water for injection (WFI), salines, transfusion solutions, physiological solutions, etc. The liquids to pro-emulsion (high viscous liquid) ratio employed during preparation of the product emulsion may vary, and in certain embodiments ranges from 0.5 to 300, such as 1 to 100, 2 to 50 or 2 to 20, and including 2 to 10. In some instances, the dosage amount of pro-emulsion formulation that is combined with the aqueous medium ranges from 100 to 1200 g, such as 300 to 600 g and the amount of aqueous medium that is combined with the dosage amount ranges from 100 to 1200 ml, such as 250 to 600 ml.

The emulsions prepared from the pro-emulsion formulations are liquid preparations that are a suspension of small particles (i.e., globules) of one liquid in a second liquid with which the first liquid will not mix. In certain embodiments, the product emulsions prepared from pro-emulsion formulations of the invention are emulsions of oil and water. As the formulations are emulsions, they are mixtures of two immiscible (e.g., unblendable) fluids, where one fluid (e.g., an oil or water) (the dispersed phase) is dispersed in the other fluid (e.g., the other of the oil or water) (the continuous phase).

The water present in the emulsions may be any convenient water, including deionized water, USP water for injection (WFI), etc.

The product emulsions include a taxane, an oil component, a surfactant component, a non-aqueous solvent component and water. In certain embodiments, the product emulsions are clear. By clear is meant that the emulsion is a translucent, if not transparent liquid, i.e., the liquid is pellucid. As such, the emulsion is not cloudy, e.g., as a suspension may appear. Further details regarding the product emulsions that may be prepared from the taxane pro-emulsion precursors are provided below. In some instances, the particle size of the final emulsion ranges from 3 to 70 nm, such as 5 to 50 nm and including 7 to 30 nm, such as 8 to 15 nm. Of interest in certain embodiments are product emulsions that are clear (e.g., as described above) and have a particle size of 70 nm or less, such as 50 nm or less, including 30 nm or less, including 25 nm or less, 20 nm or less and 15 nm or less. In some instances, any difference in particle size between the pro and product emulsions is minimal, such that the particle sizes in the pro and product emulsions are substantially the same. In some instances, any difference in particle size between the pro and product emulsions is 30 nm or less, such as 20 nm or less, 10 nm or less, 5 nm or less, 4 nm or less, 3 nm or less, 2 nm or less, including 1 nm or less.

Where desired, the pro-emulsion formulation may be stored for a period of time prior to combination with the aqueous medium. This storage time of the pro-emulsion composition may vary, where storage times may be 1 year or more, such as 2 years or more, including 3 years or more. While the storage conditions may vary, in certain instances the storage conditions are characterized by a temperature ranging from 5 to 60° C., e.g., 5° C., such as 8 to 40° C., e.g., 25° C. The activity of the taxane active agent is preserved during the storage period, such that the pro-emulsion formulations are storage stable. As such, the activity of the taxane active agent in the reconstituted product emulsion following storage is substantially the same as that in the precursor emulsion prior to being dried, where the magnitude of any difference in activity between the precursor and final emulsion may be 15% or less, such as 10% or less, including 5% or less, e.g., as measured according to HPLC performed as summarized in the following table.

| | |
|---|---|
| Measurement Wavelength | UV = 230 nm |
| Column | MERCK Lichrospher RP-18 5μ 4.0 mm ϕ × 125 mmL (ODS type) |
| Column temperature | 40° C. |
| Mobile phase | Methanol/Water 65/35 vol. % |
| Sample volume | 20 μl |
| Measurement time | PAC 13 min. DOC 20 min. |
| Internal reference | PAC butyl benzoate 0.1 mg/ml DOC isopentyl benzoate 0.1 mg/ml |

The combination protocol may vary, where agitation may be employed, e.g., by stirring, by kneading a bag that includes both the emulsion and the aqueous medium, etc.

The product taxane emulsion formulations that are produced upon reconstitution of the pro-emulsion formulation with the aqueous medium can have a physiologically acceptable pH. In certain embodiments, the pH of the emulsion formulations ranges from 2.5 to 8, such as from 3 to 7, including from 3.5 to 6. The product taxane emulsion formulations are clear formulations. The concentration of the taxane in the product emulsion may vary, ranging in some embodiments from 0.05 to 10 mg/ml, such as 0.2 to 3 mg/ml.

Methods of using the product taxane emulsion formulations include administering an effective amount of the taxane emulsion formulation to a subject in order to treat the subject for a target condition of interest. By "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom, associated with the condition being treated, such as pain. As such, treatment also includes situations where the condition is completely inhibited, e.g., prevented from happening, or stopped, e.g., terminated, such that the subject no longer experiences the condition. As such, treatment includes both preventing and managing a condition.

In practicing the methods, the emulsion formulations disclosed herein can be parenterally administered to a subject. By "parenteral administration" is meant administration by a protocol that delivers a quantity of the emulsion formulation to the subject, e.g., a patient suffering from a cellular proliferative disease, by a route other than the digestive tract. Examples of parenteral administration include, but are not limited to, intramuscular injection, intravenous injection, transdermal absorption, inhalation, and the like. In certain embodiments, parenteral administration is by injection using an injection delivery device. The amount of emulsion formulation that is administered to the subject may vary depending on a number of factors, such as patient specifics, nature of condition, nature of taxane active agent, etc. In certain embodiments, the volume of emulsion that is administered to a subject may range from 100 to 1000 ml, such as 200 to 600 ml. The time period over which this volume is administered may vary, ranging from 0.5 to 6 hr, such as from 1 to 3 hr. Dosages administered to a subject during a given procedure may also vary, ranging in some instances from 20 to 500 $mg/m^2$, such as from 50 to 300 $mg/m^2$.

In certain embodiments, the subject methods include a diagnostic step. Individuals may be diagnosed as being in need of the subject methods using any convenient protocol. In addition, individuals may be known to be in need of the subject methods, e.g., they are suffering from a target disease condition (e.g., cellular proliferative disease, prior to practicing the subject methods. Diagnosis or assessment of target condition can be performed using any convenient diagnostic protocol.

Methods of the invention may further include assessing the efficacy of the treatment protocol that includes administration of the taxane emulsion formulation. Assessing the efficacy of treatment may be performed using any convenient protocol.

Taxane emulsion formulations of the invention may be administered to a variety of different types of subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

In determining whether to administer the emulsion to a particular given subject, care will be taken to ensure that the formulation is not contraindicated for that subject. As such, symptoms of the subject may be assessed to ensure that administration of the emulsion will not have adverse effects that outweigh any benefit that that emulsion may provide.

Utility

The subject emulsion formulations and methods find use in a variety of applications, including the treatment of subjects suffering from cellular proliferative disease conditions. Cellular proliferative diseases that may be treated with compositions of the invention include, but are not limited to: carcinomas, myelomas, neuroblastomas, or sarcomas, of the brain, breast, lung, colon, prostate or ovaries, as well as leukemias or lymphomas. Specific disease conditions of interest include, but are not limited to, human ovarian cancer, breast cancer, malignant lymphoma, lung cancer, melanoma, and Kaposi's sarcoma.

Kits

Also provided are kits that find use in practicing the subject methods, as described above. For example, kits for practicing the subject methods may include a quantity of the pro-emulsion formulation, present in unit dosages, e.g., vials, or a multi-dosage format. As such, in certain embodiments, the kits may include one or more unit dosages (e.g., vials) of the pro-emulsion formulation. The term "unit dosage", as used herein, refers to physically discrete units suitable as unitary dosages for human and animal subjects, each unit containing a predetermined quantity of the subject pro-emulsion formulation calculated in an amount sufficient to produce the desired effect. The amount of the unit dosage of the subject emulsion formulation depends on various factors, such as the particular active agent employed, the effect to be achieved, and the pharmacodynamics associated with the active agent in the subject. In yet other embodiments, the kits may include a single multi-dosage amount of the emulsion formulation.

In certain embodiments, the kits may further include an amount of an aqueous medium suitable for use in reconstitution of the production taxane emulsion. The aqueous medium may be any convenient aqueous medium, such as described above, present in any suitable container, e.g., an IV bag.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., one or more pieces of paper on which the information is printed, in the packaging of the kit, in a package insert, etc. The instructions may be present on a computer readable medium, e.g., diskette, CD, DVD, etc., on which the information has been recorded. The instructions may be present on a website, which may be used via the internet to access the information at a removed site. Other convenient means are possible and may be included in the kits.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

I. Paclitaxel Formulations

A. Working Example 1

Lot. 7

200 mg of paclitaxel, 200 mg of soybean oil, 16 g of polysorbate 80, and 4 g of propylene glycol were placed into a 300 ml beaker. The beaker was heated to 50° C. and the ingredients were almost completely dissolved in an ultrasonic disperser. The beaker was then placed in a water bath with the temperature setting at 60° C. The contents were agitated with a high-speed mixer (8,000 rpm×5 min.) while adding about 50 ml of warm water at 60° C. The contents were agitated more (10,000 rpm×10 min.) to obtain a uniform solution.

16 g of propylene glycol were then added to this emulsion. The emulsion was gently stirred for more uniformity and sufficient pure water was added to make the emulsion volume be 200 ml. The pH of this solution was adjusted to around 4 with 1N hydrochloric acid or 0.1 N hydrochloric acid.

The resultant solution was poured into each 50 ml vial tube while applying nitrogen and the tube was sealed. High-pressure steam sterilization (121° C.×10 min.) was then applied. In a clean room, 50 ml of this solution was taken from the vial and poured into a 200 ml flask. The water was removed by evaporation at 60° C. to obtain a non-aqueous composition.

362 mg of the resultant non-aqueous composition was then placed into a test tube. 2 ml of pure water were added and the tube was shaken by hand for about 10 seconds to obtain a clear solution. When the particle size was measured via a particle size distribution in dynamic light scattering measurement protocol, the average size was observed to be 11.4 nm, which almost matches the average size of 11.7 nm in the solution before turning into the non-aqueous form. Regeneration of the non-aqueous composition is completed.

B. Additional Working Examples

Additional formulations and the above formulation are summarized below in Table 1.

TABLE 1

| Lot. | 1 | 2 | 3 |
|---|---|---|---|
| Drug [mg] | PAC 1 | PAC 1 | PAC 2 |
| Oil [mg] | Soybean oil 1 | Soybean oil 1 | Soybean oil 2 |
| Surfactant [mg] | Polysorbate 80 | Polysorbate 80 | Polysorbate 100 |
| Non-Aqueous solvent [mg] | PG 100 | GLY 122 | PG 122 |
| Before φ [nm] | 8.1 | 9.3 | 9.6 |
| After φ [nm] | 11.4 | 16.0 | 12.3 |

| Lot. | 4 | 5 | 6 |
|---|---|---|---|
| Drug [mg] | PAC 1 | PAC 1 | PAC 1 |
| Oil [mg] | Soybean oil 1 | Soybean oil 1 | Soybean oil 1 |
| Surfactant [mg] | Polysorbate 80 | Polysorbate 80 | Polysorbate 80 |
| Non Aqueoussolvent [mg] | PG 80 | PG 20 | 0 |
| Before φ [nm] | 9.7 | 9.7 | 9.7 |
| After φ [nm] | 10.9 | 10.1 | 10.7 |

TABLE 1-continued

| Lot. | 7 | 8 | 9 |
|---|---|---|---|
| Drug [mg] | PAC 1 | PAC 1 | PAC 1 |
| Oil [mg] | Soybean oil 1 | MCT 1 | VE 1 |
| Surfactant [mg] | Polysorbate 80 | Polysorbate 80 | Polysorbate 80 |
| Non Aqueoussolvent [mg] | PG 100 | PG 100 | PG 100 |
| Before φ [nm] | 11.7 | 11.1 | 11.6 |
| After φ [nm] | 11.4 | 11.6 | 11.6 |

In the Tables:
PAC refers to paclitaxel
Polysorbate refers to "polysorbate 80"
MCT refers to medium chain triglyceride
VE refers to Vitamin E or Tocopherol
PG refers to Propylene glycol
GLY refers to glycerin
φ refers to particle size

C. Working Example 2

Lot. 24

400 mg of paclitaxel, 200 mg of MCT, 3.2 g of polysorbate 80, 2 g of polyethylene glycol 300 (average molecule weight=300) and 160 mg of lactic acid mixture (=128 mg of lactic acid and 32 mg of 70% sodium lactate) were placed into a 50 ml beaker. The beaker was heated to 50° C. and the ingredients were almost completely dissolved in an ultrasonic disperser.

The resultant solution was poured into a 5 ml vial tube through a 0.2µ filter while applying nitrogen and the tube was sealed. The resultant solution was then heated to 95° C. for 30 min. to produce a non-aqueous composition.

30 mg of the resultant non-aqueous composition was then placed into a test tube. 4 ml of pure water were added and the tube was shaken by hand for about 20 seconds to obtain a clear solution. When the particle size was measured via a particle size distribution in the dynamic light scattering measurement protocol, the average size was observed to be 20.4 nm.

D. Additional Working Examples

Additional formulations and the above formulation are summarized below in Table 2, below:

TABLE 2

| Lot. | 21 | 22 | 23 | 24 |
|---|---|---|---|---|
| Drug [mg] | PAC 2 | PAC 2 | PAC 2 | PAC 2 |
| Oil [mg] | MCT 10 | MCT 10 | MCT 10 | MCT 1 |
| Surfactant [mg] | Polysorbate 80 | Polysorbate 80 | Polysorbate 80 | Polysorbate 16 |
| Non Aqueous solvent [mg] | PG 60 | PG 120 | PEG400 20 | PEG300 10 |
| Lactic acid mixture [mg] | 0.8 | 0.8 | 0.8 | 0.8 |
| Water [mg] | 0 | 10 | 0 | 0 |

PEG—polyethylene glycol

II. Docetaxel Formulations

A. Working Example 1

Lot. 16

150 mg of docletaxel, 150 mg of MCT, 5 g of polysorbate 80, and 3.5 g of propylene glycol were placed into a 200 ml beaker. The beaker was heated to 50° C. and the ingredients dissolved almost completely in an ultrasonic disperser. The beaker was placed in a water bath with the temperature setting at 60° C. The contents were then agitated with a high-speed mixer (7,000 rpm×2 min.) while adding about 35 ml of warm water at 60° C. The contents were then agitated more (10,000 rpm×5 min.) to get a uniform solution.

2.5 g of propylene glycol were added to this uniform solution. The solution was then gently stirred for more uniformity and sufficient pure water was added to make the volume 50 ml. The pH of this solution was adjusted to 4 with 1N hydrochloric acid or 0.1 N hydrochloric acid.

This solution was poured into each 50 ml vial tube while applying nitrogen and the tube was sealed. High-pressure steam sterilization (121° C.×10 min.) was then applied. In a clean room, 50 ml of this solution was removed from the vial and poured into a 200 ml flask. The water was removed by evaporation at 60° C. to obtain a non-aqueous composition.

452 mg of the obtained non-aqueous composition was placed into a test tube 0.2 ml of pure water was then added and the resultant composition shaken by hand for about 10 seconds to obtain a clear solution. When the particle size was measured using a particle size distribution in dynamic light scattering measurement protocol, the average size was observed to be 11.6 nm, which almost matches the average size of 11.8 nm in the solution before turning into the non-aqueous form. Regeneration of the non-aqueous composition is completed.

B. Additional Working Examples

Additional formulations and the above formulation are summarized in Table 3.

TABLE 3

| Lot. | 11 | 12 | 13 | 14 |
| --- | --- | --- | --- | --- |
| Drug [mg/ml] | DOC 1 | DOC 1 | DOC 3 | DOC 3 |
| Oil [mg/ml] | MCT 1 | MCT 1 | MCT 3 | Tocopherol 3 |
| Surfactant [mg/ml] | Polysorbate 100 | Polysorbate 80 | Polysorbate 100 | Polysorbate 100 |
| Non Aqueous solvent [mg/ml] | PG 122 | PG 80 | PG 120 | PG 120 |
| Before φ [nm] | 11.1 | 11.0 | 11.3 | 14.0 |
| After φ [nm] | 13.6 | 10.5 | 11.6 | 12.5 |

| Lot. | 15 | 16 | 17 |
| --- | --- | --- | --- |
| Drug [mg/ml] | DOC 3 | DOC 3 | DOC 3 |
| Oil [mg/ml] | Soybean oil 3 | MCT 3 | Tocopherol acetate 3 |
| Surfactant [mg/ml] | Polysorbate 100 | Polysorbate 100 | Polysorbate 100 |
| Non Aqueous solvent [mg/ml] | PG 120 | PG 120 | PG 120 |
| Before φ | 12.6 | 11.8 | 12.1 |
| After φ | 11.9 | 11.6 | 11.6 |

DOC—docetaxel

C. Working Example 2

Lot. 33

400 mg of docetaxel trihydrate, 400 mg of MCT, 9.5 g of polysorbate 80, 7 g of polyethylene glycol 300 (average molecule weight=300) and 100 mg of lactic acid mixture (=80 mg of lactic acid and 20 mg of 70% sodium lactate) were placed into a 50 ml beaker. The beaker was heated to 50° C. and the ingredients were almost completely dissolved in an ultrasonic disperser.

The resultant solution was poured into a 5 ml vial tube through a 0.2μ filter while applying nitrogen and the tube was sealed. Steam treatment (95° C.×30 min.) was then applied.

174 mg of the resultant non-aqueous composition was then placed into a test tube. 25 ml of 5% glucose solution were added and the tube was shaken by hand for about 20 seconds to obtain a clear solution. When the particle size was measured via a particle size distribution in the dynamic light scattering measurement protocol, the average size was observed to be 19.4 nm.

D. Additional Working Examples

Additional formulations and the above formulation are summarized below in Table 4:

TABLE 4

| Lot. | 31 | 32 | 33 | 34 |
| --- | --- | --- | --- | --- |
| Drug [mg] | DOC 4 | DOC-3W 4 | DOC-3W 4 | DOC-3W 4 |
| Oil [mg] | MCT 4 | MCT 4 | MCT 4 | MCT 4 |
| Surfactant [mg] | Polysorbate 100 | Polysorbate 95 | Polysorbate 95 | Polysorbate 95 |
| Non Aqueous solvent [mg] | PEG300 40 PEG400 10 | PEG300 85 | PEG300 70 | PEG300 70 |
| Lactic acid mixture [mg] | 1 | 1 | 1 | 1 |
| Heated treatment | 95° C. × 30 min. | 95° C. × 30 min. | 95° C. × 30 min. | No treatment |

DOC-3W—docetaxel trihydrate

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A non-aqueous docetaxel liquid pro-emulsion formulation comprising:

anhydrous docetaxel or a hydrate thereof;
an organic acid component in an amount ranging from 0.3 to 3% w/w, selected from the group consisting of acetic acid, lactic acid, and citric acid;
an oil component in an amount ranging from 0.5 to 5% w/w, selected from the group consisting of soybean oil, olive oil, sesame oil, corn oil, a medium chain triglyceride, and combinations thereof;
a polysorbate component in an amount of 30 to 70% w/w; and
a non-aqueous solvent component selected from the group consisting of polyethylene glycols in an amount ranging from 35 to 55% w/w,
wherein the anhydrous docetaxel or a hydrate thereof is present in an amount ranging from 0.1 to 5% w/w,
wherein the formulation does not include ethanol, and
wherein the amount of the docetaxel and the amount of the oil component differ by 50% w/w or less.

2. The pro-emulsion formulation according to claim 1, wherein the docetaxel is docetaxel trihydrate.

3. The pro-emulsion formulation according to claim 1, wherein the oil is soybean oil.

4. The pro-emulsion formulation according to claim 1, wherein the amounts of the docetaxel and oil components differ by 10% w/w or less.

5. The pro-emulsion formulation according to claim 1, wherein the polysorbate is polysorbate 80.

6. A method of administering docetaxel to a subject, the method comprising:
(a) combing the docetaxel pro-emulsion formulation according to claim 1 with an aqueous medium to produce docetaxel emulsion; and
(b) intravenously administering the docetaxel emulsion to the subject.

7. A kit comprising:
(a) the docetaxel pro-emulsion formulation according to claim 1; and
(b) an aqueous medium suitable for intravenous injection.

8. The pro-emulsion formulation according to claim 1, wherein the non-aqueous solvent component comprises polyethylene glycol 300.

9. The pro-emulsion formulation according to claim 1, wherein the oil is soybean oil or a medium chain triglyceride.

10. The pro-emulsion formulation according to claim 9, wherein
the oil is soybean oil;
the polysorbate surfactant is polysorbate 80; and
the non-aqueous solvent component comprises polyethylene glycol 300.

11. The pro-emulsion formulation according to claim 10, wherein the particle size of the formulation upon the addition to an aqueous medium, ranges from 3 to 70 nm.

12. The pro-emulsion formulation according to claim 1, wherein the polyethylene glycol has an average molecular weight of 1000 or less.

13. The non-aqueous docetaxel liquid pro-emulsion formulation of claim 1, wherein the non-aqueous docetaxel liquid pro-emulsion formulation is suitable for the preparation of an intravenously injectable composition.

\* \* \* \* \*

UNITED STATES PATENT AND TRADEMARK OFFICE
CERTIFICATE OF CORRECTION

PATENT NO. : 10,842,770 B2
APPLICATION NO. : 13/098031
DATED : November 24, 2020
INVENTOR(S) : Nabeta Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 100 days.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*